United States Patent [19]
Brosius et al.

[11] Patent Number: 5,314,331
[45] Date of Patent: May 24, 1994

[54] ORTHODONTIC SPACING SPRING

[75] Inventors: David J. Brosius, Crete; Joseph M. Sim, Edwardsville, both of Ill.

[73] Assignee: Mid-American Dental Specialties, Inc., Hickory Hills, Ill.

[21] Appl. No.: 872,592

[22] Filed: Apr. 23, 1992

[51] Int. Cl.$^5$ ............................................. A61C 3/00
[52] U.S. Cl. ......................................... 433/21; 433/149
[58] Field of Search .................................. 433/21, 149

[56] References Cited

U.S. PATENT DOCUMENTS

| | | | |
|---|---|---|---|
| 3,052,029 | 9/1962 | Wallshein | 433/21 |
| 3,837,082 | 9/1974 | Pool | 433/149 |
| 4,256,456 | 3/1981 | Wallshein | 433/21 |

OTHER PUBLICATIONS

McGann, B. Donald, "A Nickel Titanium Separating Spring", *Journal of Clinical Orthodontics*, May, 1991.

Primary Examiner—John J. Wilson
Attorney, Agent, or Firm—Leydig, Voit & Mayer, Ltd.

[57] ABSTRACT

A device for separating a pair of adjacent teeth comprising a wire spring formed from a single piece of wire. The wire spring comprises two angled leg segments connected by a bridging portion, the leg segments being offset from one another and from a central reference plane such that when the leg segments are drawn towards a common plane, the bridging portion is placed under a torsional load. This torsional load causes the legs to apply a force to the proximal walls of the adjacent teeth. The terminal ends of the leg portions are blunted, preferably through the formation of loops.

The wire utilized in formation of the separating spring is of a substantially rectangular cross section wherein the wire has a horizontal surface dimension which is greater than the vertical side dimension.

5 Claims, 3 Drawing Sheets

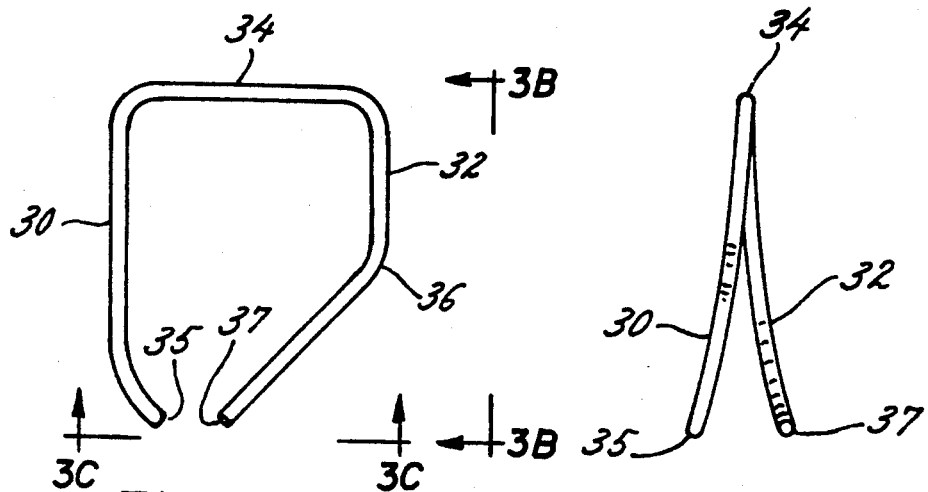
FIG 3A
(PRIOR ART)
FIG 3B
(PRIOR ART)
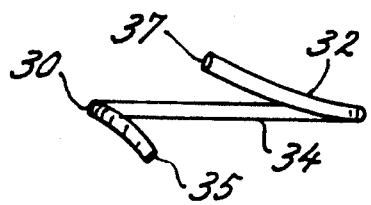
FIG. 3C
(PRIOR ART)
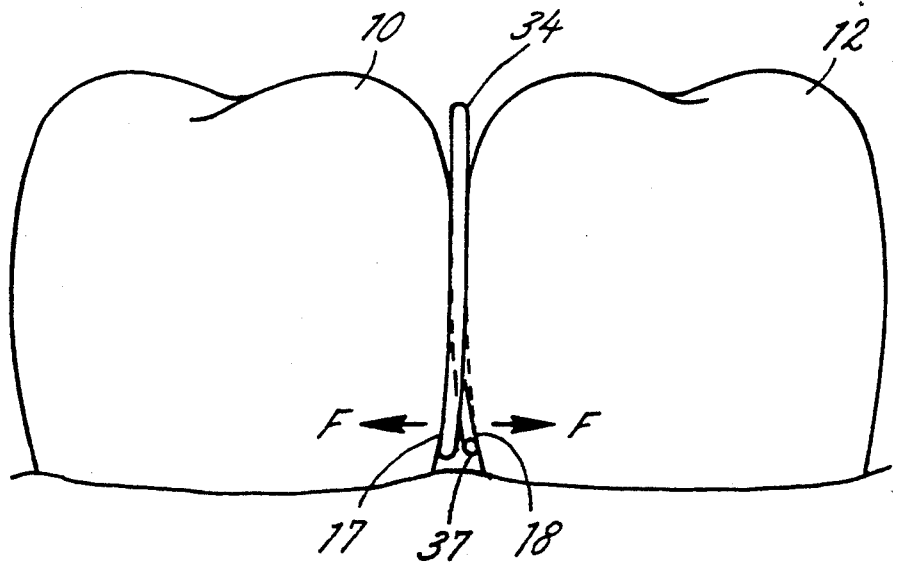
FIG. 3D
(PRIOR ART)

ORTHODONTIC SPACING SPRING

FIELD OF THE INVENTION

The present invention relates generally to orthodontic devices and specifically to spacing springs for separating teeth sufficiently to install corrective banding.

BACKGROUND OF THE INVENTION

Orthodontic treatment often requires the banding of teeth. In order to effect such banding, there must be sufficient space between adjacent teeth to permit the insertion and placement of the orthodontic bands. If adjacent teeth are too close together, it is necessary to create a space between them through the introduction of a mechanical force.

In the past, numerous devices have been utilized to create the necessary space between adjacent teeth, including elastomeric modules, twisted brass wire and metal spring devices (such as the stainless steel TP spring marketed by TP Orthodontics, Inc. of LaPorte, Ind. and the nickel titanium alloy NEET Spring marketed by PDS Products of Santa Ana, Calif.).

Each of these previously used devices has proved effective for generating the required space between adjacent teeth, but each has certain disadvantages.

Elastomeric modules work well in situations where the teeth are slightly mobile, as is often true of children. However, situations involving tight contacts may lead to the distortion or breakage of the elastomeric modules.

Twisted brass wire is effective in situations where the contact between adjacent teeth is too tight to permit the use of elastomeric modules. The use of twisted brass wire may, however, give rise to severe patient discomfort due to the application of substantial nonresilient forces. Further, the ends of the twisted wire tend to irritate the patient's interproximal gum tissue once in place.

Both the TP spring and the NEET spring may also be used in instances where the contacts are too tight for the use of elastomeric modules. However, both springs utilize a design having sharp wire ends which can irritate the patient's interproximal gum tissue both at the time of insertion and during use. These sharp ends also present a more serious patient hazard—they enhance the possibility that the device may become lodged in the patient's throat, causing choking, if aspirated. Further, if such a device is swallowed, the sharp ends can cause intestinal damage.

In addition to the fact that the previously used orthodontic springs incorporate irritating and potentially dangerous sharp end designs, these springs are also made of round wire stock, which creates an enhanced potential for occlusal interference due to the fact that the wire has the same dimensions in all directions. In other words, if the gauge of the round spring wire is increased to enhance the spacing forces provided, then, by necessity, this will also increase the extension of the wire through the occlusal plane—thereby interfering with the patient's masticatory processes.

Thus, the need exists for a spacing device which may be used in situations involving tight contacts and which will minimize irritation to patients' interproximal gum tissue and the potential for injury arising from sharp wire ends. There is also a need for a tooth spacing device having a cross section which permits spacing forces to be optimized while minimizing occlusal interference.

OBJECTS AND SUMMARY OF THE PRESENT INVENTION

It is a principle object of the present invention to provide an effective tooth spacing spring which will minimize a patient's discomfort accompanying an orthodontic spacing procedure.

It is a further object of the present invention to provide a tooth spacing spring having rounded terminal ends to minimize the potential for injury if the spring is either aspirated or ingested.

It is yet a further object of the present invention to provide a tooth spacing spring which creates minimal interference with mastication while providing effective separating forces.

Other objects and advantages of the invention will be apparent from the following detailed description.

In accordance with the present invention, a tooth spacing spring is provided which comprises a single piece of wire having a substantially straight body portion and two bent leg portions extending from opposite ends of the straight body portion. The terminal ends of the extended leg portions are blunted so as to minimize the potential for tissue damage upon insertion of the leg portions into the lingual and buccal embrasures. In a preferred embodiment of the invention, the terminal ends of the articulated legs will be blunted by forming loops at those points. The preferred embodiment of the invention further includes the use of wire stock having a rectangular cross section, rather than the round stock which has previously been used in orthodontic spring devices.

BRIEF DESCRIPTION OF THE DRAWINGS

FIGS. 3A, 3B, 3C and 3D respectively show side, end, bottom and inserted views of another prior art separating spring device;

DETAILED DESCRIPTION OF THE PREFERRED EMBODIMENTS

While the invention will be described in connection with particular preferred embodiments, it will be understood that it is not intended to limit the invention to those particular embodiments. On the contrary, it is intended to cover all alternatives, modifications and equivalents as may be included within the spirit and scope of the invention as defined by the appended claims.

Figure 1:
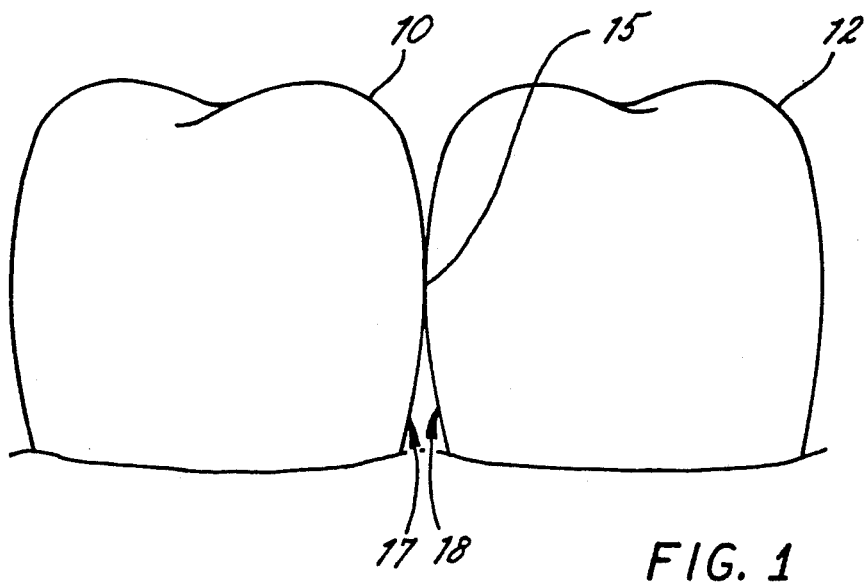
FIG. 1 is a side view of two adjacent teeth prior to undergoing a spacing procedure.

Referring now to the drawings, two adjacent teeth 10, 12 are shown generally in FIG. 1. As shown, the teeth 10, 12 are substantially in contact with one another at interface 15. As will be appreciated by one skilled in orthodontics, the teeth 10, 12 may be slightly separated from one another through the application of appropriate mechanical forces, thus permitting the application of orthodontic bands (not shown).

Appropriate separating forces may be introduced by means of a spring device inserted between the teeth. Such a spring device directs forces against the proximal walls 17, 18 of the adjacent teeth 10 and 12, respectively. The counter-directed forces generated by the spring cause the adjacent teeth 10, 12 to move slightly away from one another, thereby eliminating the contact at interface 15.

Figure 2A:
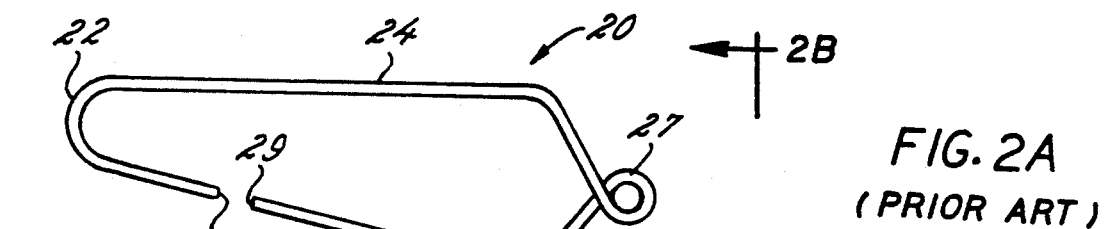
FIGS. 2A, 2B and 2C respectively show side, end and bottom views of a prior art separating spring device.
Figure 2C:
Figure 2B:
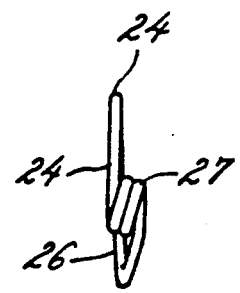

FIGS. 2A, 2B and 2C show various views of a known separating spring 20, marketed as the TP spring by TP Orthodontics, Inc. of LaPorte, Ind. As may be seen, the TP spring has a first leg section 22 for insertion in the lingual embrasure, a bridge section 24 which traverses the occlusal plane and a second leg section 26 for insertion in the buccal embrasure. The separating forces generated by the TP spring are due primarily to the width of the wire forming the spring. That is, when the TP spring 20 is inserted between the adjacent teeth 10, 12 a space will be generated due to the wedging action of the device. When the TP spring 20 is placed between the adjacent teeth 10, 12, the spring is placed under a compressive stress at any point where the diameter of the wire exceeds the width of the interproximal gap. Accordingly, as the spring element seeks to relieve this compressive stress, a counter-directed force is applied against the proximal walls 17, 18 of the adjacent teeth 10, 12, thereby forcing those teeth apart.

During insertion of the TP spring 20, the first leg section 22 is typically inserted into the lingual embrasure. Following the insertion of the first leg section 22, the remainder of the spring is wrapped around the contact point 15 (FIG. 1) and the second leg section 26 is inserted into the buccal embrasure. During this wrapping procedure, the second leg section 26 may be bent slightly so as to adapt to the particular geometry of the interproximal gap between adjacent teeth 10, 12. In order to facilitate this bending, the TP spring is provided with an integral coil 27. As will be appreciated by those skilled in orthodontics, the use of such a coil permits leg section 26 to be manipulated without imparting bending stresses to the remainder of the device.

In the TP spring 20, the terminal ends 28, 29 of leg portions 22 and 26, respectively, may be quite sharp. As will be recognized, these sharp ends may cause significant patient discomfort both at the time of insertion and during use, due to irritation of the interproximal gum tissue. In addition to this irritation, the sharp ends 28, 29 may get caught on the relatively soft enamel of the teeth during the insertion procedure, thus making the procedure more difficult. Further, the sharp ends of the TP spring present a significant hazard should the device become dislodged during use and be either aspirated or swallowed.

The TP spring is composed of a single piece of stainless steel wire having a substantially round cross section. As will be recognized by those skilled in the art, the use of such wire may give rise to increased patient discomfort due to the low ductility of the stainless steel. In addition, as will be appreciated by those skilled in the art, the use of round wire stock may cause interference with mastication due to the high profile of the wire across the occlusal plane.

A second spring device that has been used by orthodontists is the McGann NEET spring marketed by PDS Products of Santa Ana, Calif. Side, end and bottom views of the NEET spring are illustrated, respectively, in FIGS. 3A, 3B and 3C. The disposition of the NEET spring between adjacent teeth is shown in FIG. 3D. As shown in the side view of FIG. 3A, the NEET spring has a first leg segment 30, a second leg segment 32, and a substantially straight bridge segment 34 connecting the first and second leg segments 30, 32. As seen most clearly in the end view of FIG. 3B and the bottom view of FIG. 3C, the legs 30, 32 diverge from one another.

The first leg segment 30 of the NEET spring is provided with a hook-like end 35, and the second leg segment 32 has a sharp bend 36 which directs the terminal end 37 of the second leg 32 towards the first leg 30.

In practice, the terminal hook 35 of the first leg 30 is inserted into either the lingual or buccal embrasure. The spring is then stretched over the contact point 15 (FIG. 1) between the adjacent teeth 10, 12 (as seen in FIG. 3C) and the terminal end 37 of the second leg 32 is inserted into the buccal embrasure. The separating force F of the NEET spring is generated by means of the torsion created within the bridge segment 34 of the spring body as the divergent legs 30, 32 are forced into near alignment between the teeth 10, 12. This separating force is directed against the proximal walls 17, 18 of the adjacent teeth 10, 12, thereby forcing the teeth apart.

As with the TP spring, the terminal ends 35, 37 of the NEET spring are sharp-ended wire. This sharp ended design may lead to patient discomfort due to abrasion of the interproximal tissue. Further, as discussed previously, the sharp-ended design may lead to serious injuries if the device is accidentally aspirated or swallowed. Like the TP spring, the NEET spring is comprised of round wire stock. Hence, an unnecessary degree of interference with mastication may be encountered due to the relatively high profile of the wire at the occlusal surface.

Figure 4A:
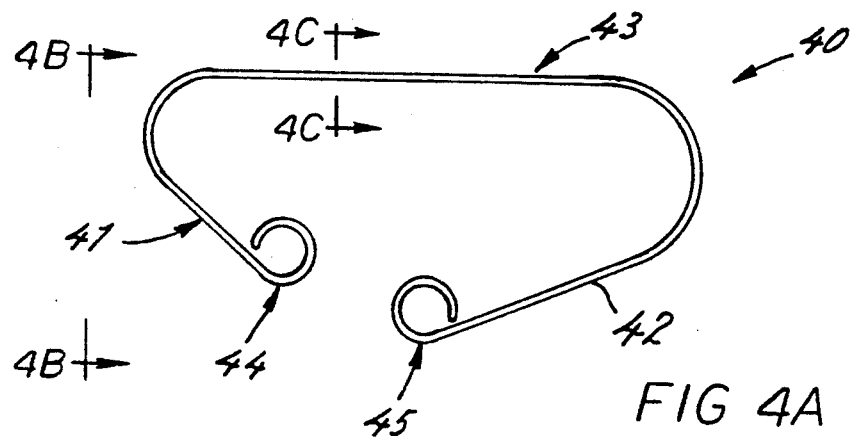
FIG. 4A shows a profile view of the separating spring of the present invention.
Figure 4B:
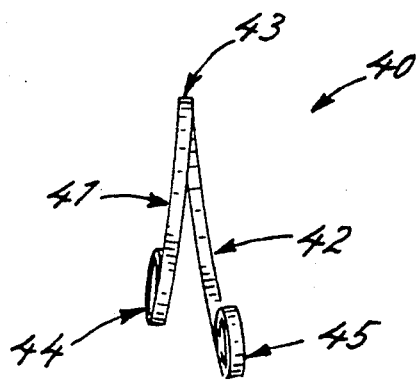
FIG. 4B shows an end view of the separating spring of the present invention.

The tooth separating spring 40 of the present invention is illustrated in side view in FIG. 4A and in end view in FIG. 4B. As illustrated, the spring of the present invention comprises a first leg portion 41, a second leg portion 42 and a bridging segment 43 disposed between first and second leg portions 41, 42. As with the NEET spring, the first and second leg portions 41, 42 diverge from one another—as well as from a central vertical reference plane defined by the lingual embrasure, the buccal embrasure and the contact point 15 (FIG. 1) between the adjacent teeth 10, 12.

Due to the normal divergence between the first and second leg portions 41, 42, a torsional load is generated within bridging segment 43 when leg portions 41, 42 are forced into near alignment along a common vertical reference plane. Accordingly, when the spacing spring of the present invention is inserted into the interproximal gap, a separating force will be directed against the proximal walls of the teeth 10, 12 (FIG. 1) by the legs 41, 42 as the spring attempts to relieve the torsion in the bridging segment 43.

In accordance with an important aspect of the present invention, the terminal end of the leg portions 41, 42 have a rounded (or blunted) configuration. In the preferred embodiment, this blunting is achieved by means of integrally formed loops 44, 45 formed at the terminal ends of first and second leg portions 41 and 42, respectively. These loops are formed by conventional wire bending processes.

As will be readily recognized, the terminal loops 44, 45 significantly reduce the potential for patient discomfort due to abrasion of the interproximal gum tissue. Further, the rounded ends 44, 45 of the present invention substantially eliminate the potential for serious injury if the device is either aspirated or swallowed. If the spring 40 is swallowed, the rounded ends will permit passage through the digestive tract without substantial danger of intestinal damage. Similarly, if the separating spring 40 of the present invention is aspirated, the rounded configuration will facilitate natural removal through coughing due to the reduced likelihood of the spring becoming caught within the patient's airway.

Figure 4C:
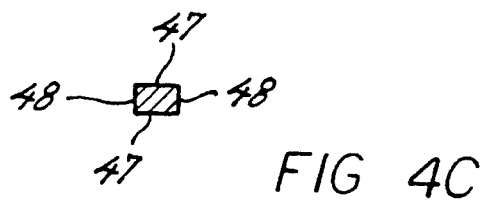
FIG. 4C shows a cross section through FIG. 4A.

In accordance with another aspect of the preferred embodiment of the invention, the spacing spring 40 is formed from a single piece of nickel titanium alloy wire, which wire has a rectangular cross section (as illustrated in FIG. 4C). As shown in cross section, the rectangular wire has horizontal surface portions 47 and vertical side portions 48. In the preferred embodiment, the width of the surface portion 47 is greater than the depth of the side portion 48. When the inventive spring is applied, the wire is, therefore, orientated such that the surface portions 47 substantially span the gap between the teeth 10, 12 while the side portions 48 are located adjacent the proximal walls of the teeth 10, 12 to be separated.

It will be appreciated that utilizing a rectangular wire permits the fabrication of a spacing spring 40 with sufficient resilience to effect movement of the adjacent teeth 10, 12 while at the same time minimizing occlusal interference. As discussed previously, known spacing springs have utilized round wires, typically having a gauge of approximately 0.018 inches. In contrast, in the present invention, the wire utilized has a width (horizontal surface dimension) ranging between 0.020 and 0.024 inches (preferably 0.022 inches) and a depth (vertical side dimension) ranging between 0.014 and 0.018 inches (preferably 0.016 inches). Accordingly, greater separating forces are provided than in the previously-used round wire separating springs and yet the wire sits lower on the occlusal plane, thereby substantially reducing interference with mastication.

As can be seen from the foregoing detailed description, this invention provides an effective tooth spacing spring which will minimize a patient's discomfort during an orthodontic spacing procedure. The spacing spring utilizes rounded terminal ends which reduce the potential for irritation of the interproximal gum tissue as well as reducing the potential for injury if the device is either aspirated or swallowed. Further, the wire utilized in the spring of the present invention is of a substantially rectangular configuration, thereby creating minimal interference with mastication while maintaining effective separating forces.

We claim as our invention:

1. A wire spring device for use in separating adjacent teeth, said spring device comprising a single piece of wire having a first leg portion for insertion into the lingual embrasure, a second leg portion for insertion into the buccal embrasure and a bridge portion connecting said first and second leg portions, said first and second leg portions being offset from one another and from a central reference plane such that a torsional load is created within said bridge portion when said first and second legs are drawn towards said central reference plane and inserted between the adjacent teeth, thereby applying a separating force to said teeth as said first leg portion acts against the proximal wall of one of the adjacent teeth and said second leg portion acts against the proximal wall of the other of the adjacent teeth, said wire having a substantially rectangular cross section defining a horizontal surface dimension and a vertical side dimension with the horizontal dimension being greater than the vertical dimension, said device being configured such that when it is inserted between the teeth, the vertical dimension of said wire lies adjacent the proximal walls of the teeth and the horizontal dimension lies in a plane spanning the interproximal gap between the teeth and wherein the vertical dimension determines the thickness of said wire above the occlusal surface of the teeth.

2. The spring device of claim 1 wherein the terminal ends of the first and second leg portions are blunted.

3. The spring device of claim 2 wherein said blunted terminal ends are of a looped configuration.

4. The spring device of claim 1 wherein the horizontal surface dimension is in the range of 0.020–0.024 inches and the vertical side dimension is in the range of 0.014–0.018 inches.

5. The spring device of claim 1 wherein said wire is composed of a nickel titanium alloy.

* * * * *